United States Patent [19]

Kurek

[11] Patent Number: 5,225,597

[45] Date of Patent: Jul. 6, 1993

[54] SELECTIVE, HIGH PURITY PREPARATION OF N-MONOALKYL ALKYLENEDIAMINES

[75] Inventor: Paul R. Kurek, Barrington, Ill.

[73] Assignee: UOP, Des Plaines, Ill.

[21] Appl. No.: 852,361

[22] Filed: Mar. 13, 1992

[51] Int. Cl.$^5$ .......................................... C07C 209/04
[52] U.S. Cl. .................................. 564/446; 564/461; 564/472; 564/473; 564/498; 564/499; 564/511
[58] Field of Search ............... 564/472, 473, 498, 499, 564/461, 511, 446

[56] References Cited

U.S. PATENT DOCUMENTS 3,707,563  12/1972  Pikl ......................................... 564/473
4,217,308  8/1980  Benady et al. ......................... 564/498

FOREIGN PATENT DOCUMENTS 2082172  3/1982  United Kingdom ................ 564/498

Primary Examiner—Allen J. Robinson
Assistant Examiner—Scott C. Rand
Attorney, Agent, or Firm—Thomas K. McBride; Eugene I. Snyder

[57] ABSTRACT

A continuous method of preparing N-monoalkyl alkylenediamines, uncontaminated by the N,N'-dialkyl alkylenediamine, is based on the observation that the disubstituted material selectively precipitates from aqueous media. A scheme is presented where an aqueous alkylenediamine is reacted with a suitable carbonyl component and hydrogen over a supported platinum catalyst. Where the alkylenediamine forms an azeotrope with water it can be conveniently recycled to the reactor.

19 Claims, 1 Drawing Sheet

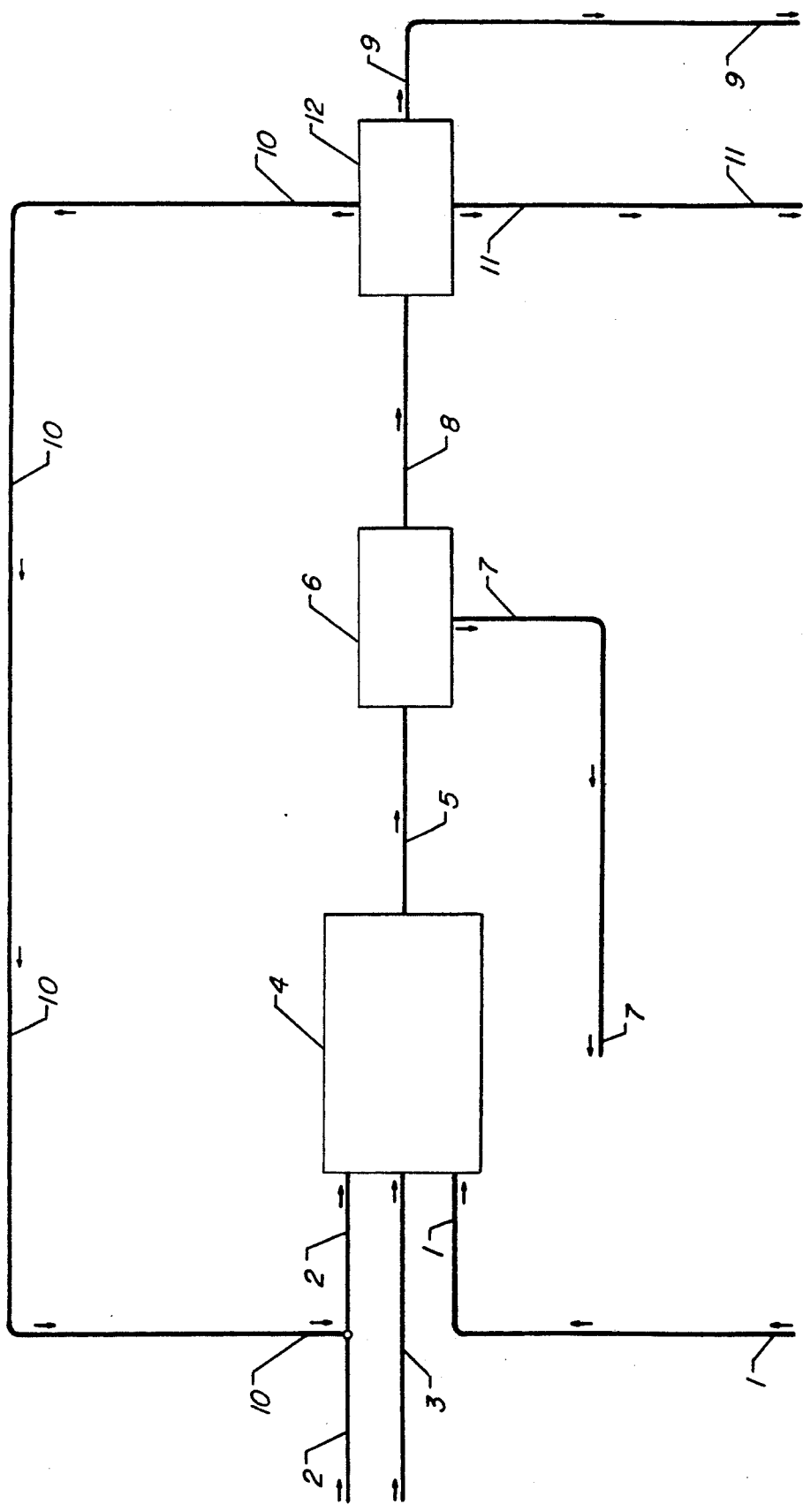

SELECTIVE, HIGH PURITY PREPARATION OF N-MONOALKYL ALKYLENEDIAMINES

BACKGROUND OF THE INVENTION

N-monoalkylated alkylenediamines, and particularly N-monoalkylethylene diamines, especially where the alkyl is a cycloalkyl group, have found use as corrosion inhibitors, fuel additives, stabilizers for resins, and agents for the purification of acrylic monomers. To date no continuous methods for their preparation appear to have been reported. The preparative route to these materials commonly utilizes the reaction of a carbonyl compound (an aldehyde or ketone) with an alkylenediamine to afford the Schiff base, which is an imine, and subsequent hydrogenation of the imine functionality of the Schiff base to the corresponding amine, as is exemplified below by the reaction of cyclohexanone with ethylenediamine,

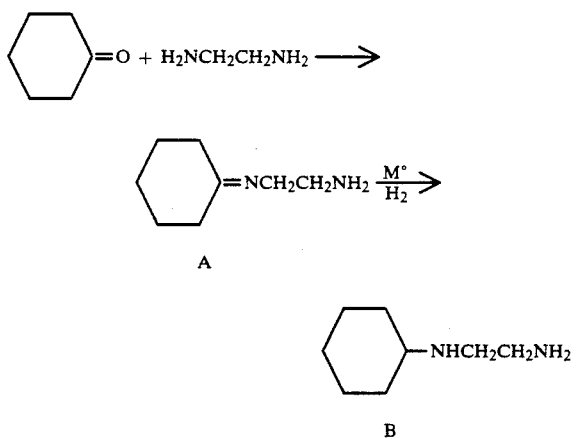

where $M^o$ is a zerovalent metal used as a hydrogenation catalyst, such as nickel, palladium, platinum, and so forth. [Although the foregoing equation may be somewhat of a simplification of the actual reactions occurring it suffices for the purpose of pointing to the salient characteristics important to this discussion.]

The foregoing reaction is attended by the side reaction,

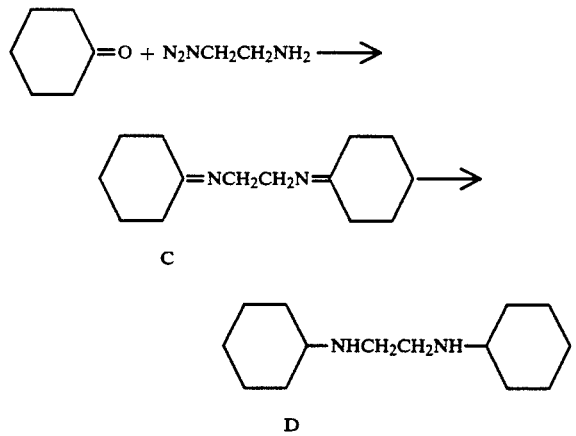

which is significant for several reasons. Where one desires only pure monoalkylated product B the formation of the dialkylated material D now imposes a purification stage which in itself may prove cumbersome at best and which may substantially add to the cost of producing pure B, as for example by substantially decreasing the yield of pure monoalkylated product. In such a case one then may be faced with the conundrum of effecting the reaction under conditions of low conversion to avoid or to minimize dialkylated product formation, or one may push conversion to higher limits while forming more of the dialkylated product and necessitating more extensive purification.

The side reaction is also significant for its detrimental effect on the hydrogenation catalyst, especially where the process is conducted in a continuous mode. The diimine C is an excellent complexing agent for those metals which are commonly used as a hydrogenation catalyst, such as nickel and palladium. Consequently these metals are slowly but continuously leached, leading to a gradual loss of selectivity and activity as well as to metal loss. The leached metal may ultimately appear in the N-monoalkylated product where it also may be detrimental to product stability, or interfere with the intended use of the product.

We have found a means to avoid the foregoing problems and have devised a process for the preparation of a high purity N-monoalkyl alkylenediamine where the process is adaptable to a continuous mode. More particularly, we have found that if the alkylenediamine and the carbonyl compound are reacted in an aqueous system, the dialkylated product (i.e., N,N'-dialkyl alkylenediamine) is only sparsely soluble in the cooled product mixture and may be readily removed to thereby afford high purity (95+%) monoalkylated product, N-alkyl alkylenediamine, upon removal of unreacted materials from the product mixture. Secondly, we have found that platinum appears unique in its resistance to extraction by materials like C, the diimine, and consequently can be safely used without substantial loss in a continuous process. Our invention is grounded on these observations.

SUMMARY OF THE INVENTION

The object of my invention is to continuously prepare N-monoalkyl alkylenediamines in high purity with good selectivity at high conversions. An embodiment comprises reacting an aldehyde or ketone with an excess of an alkylenediamine in an aqueous system in the presence of hydrogen and a hydrogenation catalyst, cooling the resulting product mixture and removing the dialkylated product which separates therefrom, and recovering pure (95+%) N-monoalkyl alkylenediamine therefrom after distillation of unreacted alkylenediamine and water. In a particular embodiment the diamine is ethylenediamine. In a still more particular embodiment the carbonyl compound is cyclohexanone. In yet another specific embodiment ethylenediamine is present at from 1 to about 6 molar proportions relative to the carbonyl compound and water is present in from 10 to about 20 weight percent of the alkylenediamine-water mixture. In still another embodiment an azeotrope of ethylenediamine in water is distilled from the product mixture and recycled to the reactor. Other purposes and embodiment will become apparent from the following description.

DESCRIPTION OF THE FIGURE

FIG. 1 depicts a process flow according to this invention.

DETAILED DESCRIPTION OF THE INVENTION

There are two keys to our invention. One is the discovery that the N,N'-dialkyl alkylenediamines are only sparsely soluble in an aqueous alkylenediamine mixture at ambient temperature relative to the solubility of the corresponding N-monoalkyl alkylenediamine. Another key discovery is that platinum is quite resistant to extraction by diimines, which are good complexing agents for other hydrogenation catalysts, and platinum may therefore be safely utilized in a continuous process without excessive loss.

The reaction products of this invention result from the condensation of a carbonyl compound which is either an aldehyde or a ketone and an alkylenediamine to afford an imine as an intermediate. Under reaction conditions the imine is readily hydrogenated to yield the alkylated alkylenediamines as the reaction products. The alkylenediamines of this invention may be represented by the formula $H_2N(CH_2)_xNH_2$, where $x=2-10$. Ethylenediamine ($x=2$) is an especially preferred diamine in the practice of this invention not only for the nature of the products formed but also for the properties of its azeotropic mixture with water. However, the invention as claimed has many variants and also may be utilized for the higher alkylenediamines, especially those where $x=3-6$.

As shown in the previous equations, a carbonyl compound in the form of an aliphatic aldehyde or ketone is reacted with the alkylenediamine to form a Schiff base, or imine, as an intermediate to ultimately afford as the desired product the N-alkyl alkylenediamine of formula $RNH(CH_2)_xNH_2$. The aliphatic aldehyde and ketones which may be used in the practice of this invention are those having from 3 up through about 10 carbon atoms. Examples of aldehydes which may be used include propanal, butanal, pentanal, hexanal, octanal, nonanal, decanal, and their branched counterparts. The ketones which may be used in the practice of this invention are aliphatic ketones, particularly those containing from 3 to 10 carbon atoms, and especially the cycloaliphatic ketones having from 5 through about 10 carbon atoms. Examples include materials such as acetone, butanone, 2-pentanone, 3-pentanone, 2-hexanone, 3-hexanone, 2-heptanone, 3-heptanone, 4-heptanone, the octanones, nonanones, and decanones, and their branched counterparts. Illustrative of the cyclic ketones are the unsubstituted ones such as cyclopentanone, cyclohexanone, cycloheptanone, cyclooctanone, cyclononanone, and cyclodecanone, as well as alkyl-substituted cycloaliphatic ketones such as methylcyclopentanone, ethylcyclopentanone, propylcyclopentanone, butylcyclopentanone, pentylcyclopentanone, dimethylcyclopentanone, diethylcyclopentanone, methylcyclohexanone, ethylcyclohexanone, propylcyclohexanone, butylcyclohexanone, ethylmethylcyclohexanone, dimethylcyclohexanone, methylpropylcyclohexanone, and so forth.

The moiety R in the final product $RNH(CH_2)_xNH_2$ formally arises by replacement of the carbonyl oxygen by a single hydrogen atom. Where an aldehyde is a reactant, R is necessarily a primary alkyl group, but where a ketone is a reactant R is necessarily a secondary alky group. Exemplary, but not exhaustive, of R as originating from aldehydes is 1-propyl, 1-butyl, 1-pentyl, 1-hexyl, 1-heptyl, 1-octyl, 1-nonyl, and 1-decyl, along with their branched counterparts as, for example, 2-methyl-1-propyl, 2-methyl-1-butyl, 3-methyl-1-butyl, 2,3-dimethyl-1-butyl, and so forth. Where R originates from a ketone the alkyl group is exemplified by isopropyl, sec-butyl, and any one of the isomeric secondary pentyl, hexyl, heptyl, octyl, nonyl, and decyl groups. Also included are such cyclic moieties as cyclopentyl, cyclohexyl, cycloheptyl, cyclooctyl, etc., and their substituted counterparts.

The carbonyl-containing component and an ethylenediamine (as representative of the alkylenediamines)-water mixture is used as a feedstock along with hydrogen for a reactor where all components are brought into contact with a hydrogenation catalyst. Within the reactor several reactions occur, the first of which is the reaction of the carbonyl component with the diamine to afford an imine in the case where only one of the primary amino groups reacts, and, less desirably, the diimine in the case where both of the primary amino moieties react. The mole ratio of the diamine to the aldehyde or ketone can range from 1:1 up to about 6:1. Increasing the mole ratio increases the conversion of the carbonyl component and tends to minimize diimine formation. However, as for all cases where one component is used in large excess, a high ratio imposes economic penalties whether or not the excess is recovered. In the case where ethylenediamine is used the optimum molar proportion of diamine to carbonyl component seems to be in the range of 4.5-5.5 for maximum conversion and selectivity while minimizing economic penalties.

As previously noted a key to our invention is the use of an aqueous diamine in the reactor feedstock in order to facilitate separation of any formed N,N'-dialkyl alkylenediamine in the reactor. Where the diamine is ethylenediamine it has been found that a weight ratio of amine to water from about 10:1 through as low as about 4:1 is preferred. We note that an aqueous ethylenediamine having about a 4:1 weight ratio of imine to water corresponds approximately to the composition of the ethylenediamine-water azeotrope. Certainly where the ethylenediamine is recycled from the reaction mixture to the reactor there is no advantage in having a smaller weight ratio of diamine to water than that which is found in its azeotropic mixture.

The second reaction which occurs in the reactor is the reduction of the imine linkage to the amino linkage, i.e., $C=N \rightarrow CH-NH$, brought about by gaseous hydrogen in the presence of zerovalent platinum acting as a hydrogenation catalyst. Hydrogen may be present at a pressure anywhere from atmospheric up through several thousand pounds per square inch. The principal effect of hydrogen partial pressure is on the rate of hydrogenation. It is desirable that the imine be hydrogenated as quickly as possible after formation in order to minimize other side reactions. Consequently, the particular pressure of hydrogen in the reactor will depend upon such things as reaction temperature, liquid hourly space velocity of the reactants, equipment limitations, and so forth. It is found that hydrogen partial pressures on the order of 200 to 1500 psig are convenient ones at which to work. However, it needs to be emphasized that the partial pressure of hydrogen is not a particularly crucial variable in the success of my invention and an appropriate value is readily determined by the skilled worker.

The reaction generally is conducted in the range between about 150° and 225° C. It has been noted that decomposition tends to occur at temperatures much in excess of 225° C. It also has been noted that the reaction proceeds too slowly, for commercial purposes, at a temperature under about 150° C. Consequently, the range between about 175° and 200° C. is preferred.

As previously mentioned the hydrogenation catalyst used in the practice of this invention is a supported zerovalent platinum. The nature of the support is not particularly critical although platinum supported on carbon (charcoal) has proved to be rather useful. However, other supports should be considered as essentially interchangeable, including materials such as alumina, clays, titania, boria, and so forth. However, it is to be noted that since the feedstock is an aqueous system the support must be hydrothermally stable as well as one which does not swell and tend to interfere with feedstock flow in the presence of water. The concentration of platinum on the support also is not a particularly sensitive variable and catalysts using about 1% on platinum have been found quite adequate. Certainly lower concentrations of platinum, even down to 0.01%, may be used although one could expect a loss in activity at such levels. Higher concentrations, even up to 5% and more, also can be used although the gain in productivity may not be commensurate with the increased platinum loading.

The diamine and carbonyl components are reacted in an aqueous system in the presence of hydrogen and a zerovalent platinum hydrogenation catalyst to give a mixture of monoalkylated and dialkylated diamine via reduction of the intermediate monoimine and diimine, resp. Water is formed as the reaction proceeds, and therefore the effluent from the reactor is more highly aqueous than the feedstock to the reactor. The reactor effluent is then cooled, with the effect that the dialkylated product, $RNH(CH_2)_2NHR$, [again using ethylenediamine as a representative example] separates from the aqueous product mixture. The dialkylated diamine is only sparingly soluble in aqueous ethylenediamine, at or near ambient temperature, which is one of the reasons for conducting the reaction in the presence of water. The dialkylated product which separates from the cooled product mixture is then removed to afford a product mixture depleted in N,N'-dialkyl ethylenediamine and which is composed essentially of an aqueous ethylenediamine solution of the monoalkylated product, N-monoalkyl ethylenediamine or, more generally, N-monoalkyl alkylenediamine.

The reaction mixture is then distilled to remove the ethylenediamine, primarily as an azeotrope with water. Since both water and ethylenediamine have boiling points less than the ethylenediamine-water azeotrope, the following will occur. If the product mixture contains excess water-that is, if there is more water present than is necessary to distill all of the ethylenediamine as an azeotrope-the excess water will first be removed upon distillation followed by the ethylenediamine-water azeotrope. If excess ethylenediamine is present-that is, more ethylenediamine is present than is necessary to form the azeotrope with all of the water present-then ethylenediamine will first appear in the distillate followed by the ethylenediamine-water azeotrope. And in those cases where the ethylenediamine:water ratio equals that found in the azeotropic composition, then only the ethylenediamine-water azeotrope will be distilled. But in any case, ultimately all of the ethylenediamine and water will be removed to afford the monoalkylated product with less than, and usually considerably less than, 5% of the dialkylated product.

One desirable variant is depicted in FIG. 1, where the alkylenediamine recovered from the cooled product mixture is recycled to the reactor. Hydrogen is admitted to the reactor at 1 along with the carbonyl component 2 and an aqueous diamine at 3. In practice the reaction between the carbonyl and the diamine components of this invention is often so rapid that these components are fed to a premixer where initial reaction occurs, and the initial product mixture which forms is thereafter conducted to the reactor. As noted before, the molar ratio of diamine to aldehyde or ketone may range from as low as 1 up through as high as about 6, but generally is in the range of 4.5 through 5.5. The water present in the aqueous mixture is such as to give a diamine:water weight ratio of between 10:1 and about 4:1. In any event, all the reactants, whether or not pre-reacted, enter reactor 4.

The reaction mixture in the reactor behaves as if there is selective formation of the monoimine which is virtually immediately reduced in reactor 4 by hydrogen with the aid of a supported zerovalent platinum catalyst also present in 4. Reactor effluent 5 then is passed to a heat exchanger or cooler 6 where the product mixture is cooled from the temperatures used in reactor 4 (150°-225° C., and usually between 175°-200° C.) in order to effect separation of the N,N'-dialkyl alkylenediamine because of its relatively low solubility in aqueous solvents. The unwanted dialkylated product is removed at 7 and the cooled product mixture is passed into a distillation column 12 which effects separation of water at 9 and ethylenediamine at 10 to afford as bottoms the desired monoalkylated product at 11. The recovered alkylenediamine, which may be removed at least in part as an azeotrope, then is recycled to the reactor as indicated. The composition of the product stream 11 is such as to have under, and generally substantially under, 5% of the dialkylated product.

It is not necessary for the success of this invention for the alkylenediamine to form an azeotrope with water. However, since an aqueous alkylenediamine feedstock is desired in the practice of this invention it is readily seen that such an azeotrope is also a highly beneficial aspect of our invention. It is for this reason that ethylenediamine is particularly favored in the practice of our invention.

The following examples are only illustrative of my invention which should not be limited thereto or curtailed thereby in any manner. The examples are not intended to be exhaustive but are intended solely to illustrate some of the characteristics of my invention.

EXAMPLE 1

Batch procedure for the preparation of N-cyclohexyl ethylenediamine (CEDA)

To a 850 cc glass liner for a rotating autoclave was charged 12.25 g (0.125 mole) cyclohexanone, 3.7 g of a catalyst consisting of 0.3 weight percent platinum (sulfided) on alpha alumina, and an 80 weight percent solution of ethylenediamine in de-ionized water (37.5 g (0.63 mole) ethylenediamine and 9.37 g (0.52 mole) water). An exotherm was generated immediately associated with the formation of Schiff bases from the reaction of cyclohexanone and ethylenediamine. The liner was placed into a rotating autoclave, purged with nitrogen, charged to 1,000 psig with hydrogen or 500 psig each of hydrogen and nitrogen, and then the autoclave was rotated at approximately 30 rpm for 6-8 hours at 160°–180° C. The cooled liner was vented, flushed with nitrogen to avoid catalyst ignition, and the cooled product mixture was removed to afford a clear to pale yellow viscous liquid containing some solids which were principally N,N'-dicylohexyl ethylenediamine (DICEDA). The product mixture was filtered through diatomaceous earth to remove catalyst and DICEDA, and the resulting filtrate contained, in addition to unreacted ethylenediamine, CEDA with only traces of DICEDA. The liner and filter cake were rinsed with methanol and subsequent removal of volatile material at 80° C. afforded product which was principally DICEDA. Removal of volatiles at 80° C. at 30 inches vacuum afforded 15 grams CEDA. Conversion of cyclohexanone amounted to 99+% with a 95% yield of CEDA and 5% DICEDA.

EXAMPLE 2

Solubility of DICEDA in aqueous media

A mixture of 60 g. ethylenediamine (EDA), 15.1 g water, 23.1 g CEDA and 1.2 g DICEDA was prepared to approximate a final reaction product mixture. This mixture was heated to make it homogeneous and then analyzed by gas chromatography using the percentage areas of each of the well-separated components relative to that of ethylenediamine which was set to 100. The area percents of CEDA and DICEDA were 32.6 and 2.74, respectively. The same mixture was cooled to ambient temperature (ca. 20° C.), solids were removed by filtration, and the filtrate analyzed similarly. The area percents of CEDA and DICEDA were 31.0 and 0.61, resp. These results show that about 80% of the DICEDA precipitated as a solid and was removed.

EXAMPLE 3

Continuous preparation of N-cyclohexyl ethylenediamine; general procedure

Feedstocks of cyclohexanone and of (aqueous) ethylenediamine were premixed to form a complex Schiff base mixture which then was passed downflow over a fixed catalyst bed in a reaction zone approximately ⅜×8¾ inches in a hydrogen atmosphere at about 1,000 psig total pressure. Samples of the effluent (reaction product mixture) were analyzed periodically as the reaction variables were changed to determine the response of the system to process changes.

In this example the ratio of ethylenediamine:cyclohexanone, the reaction temperature, and the H₂:feed ratio were varied using as a catalyst 0.3 weight percent platinum (sulfided) on gamma-alumina in a non-aqueous environment. Samples were taken every 6 hours to afford the results in Table 1.

TABLE 1

| Effect of Process Variables on Conversion and Selectivity | | | | | |
|---|---|---|---|---|---|
| Peri- | Mole Ratio | Temp. | Conversion[b] | Selectivity | |
| od | EDA:ketone[a] | °C. | (mole %) | CEDA | DICEDA |
| 1 | 5:1 | 181 | 99.6 | 55.2 | 1.8 |
| 2 | 5:1 | 180 | 98.6 | 96.7 | 3.2 |
| 3 | 5:1 | 178 | 99.5 | 97.8 | 2.2 |
| 4 | 5:1 | 177 | 99.6 | 96.4 | 3.6 |
| 5 | 5:1 | 180 | 99.7 | 96.8 | 2.7 |
| 6 | 5:1 | 180 | 99.7 | 97.4 | 2.6 |
| 7 | 3:1 | 185 | 99.7 | 80.5 | 4.3 |
| 9 | 3:1 | 180 | 99.7 | 91.1 | 4.4 |
| 10 | 3:1 | 181 | 99.8 | 80.9 | 4.1 |
| 12 | 1:1 | 176 | 99.7 | 89.9 | 5.5 |
| 13 | 1:1 | 178 | 99.7 | 85.1 | 4.5 |
| 15 | 5:1 | 180 | 99.7 | 97.3 | 2.7 |

TABLE 1-continued

| Effect of Process Variables on Conversion and Selectivity | | | | | |
|---|---|---|---|---|---|
| Peri- | Mole Ratio | Temp. | Conversion[b] | Selectivity | |
| od | EDA:ketone[a] | °C. | (mole %) | CEDA | DICEDA |
| 17 | 5:1 | 180 | 99.7 | 97.2 | 2.8 |
| 20 | 5:1 | 180 | 99.7 | 96.1 | 3.9 |
| 22 | 5:1 | 175 | 99.7 | 96.6 | 3.4 |
| 23 | 5:1 | 190 | 99.7 | 94.7 | 5.2 |
| 24 | 5:1 | 200 | 99.7 | 96.2 | 3.7 |
| 25 | 5:1 | 199 | 99.7 | 94.8 | 5.2 |
| 26 | 5:1 | 201 | 99.7 | 96.1 | 3.8 |
| 27 | 5:1 | 200 | 99.7 | 96.3 | 3.7 |
| 28 | 5:1 | 200 | 99.7 | 96.3 | 3.7 |

[a]Ketone was cyclohexanone.
[b]Conversion of cyclohexanone

Optimum results appeared to be attained at a diamine:ketone ratio of about 5:1 within the temperature interval of 180°–200° C. Although the foregoing results were obtained in a non-aqueous medium, similar results could be achieved in an aqueous medium.

EXAMPLE 4

Continuous preparation of N-cyclohexyl ethylenediamine

This run was performed in a manner similar to that above with a catalyst of 0.3 weight percent palladium on theta-alumina and an aqueous ethylenediamine feedstock where the weight ratio of EDA to water was 4:1. Results are tabulated in Table 2, which shows that the catalyst deactivated noticeably in a time period within which a platinum catalyst showed virtually unchanged activity. In general, the data show that the selectivity to CEDA is inferior to that obtained with a platinum catalyst. At period 22 the cyclohexanone was diluted 1:1 with isopropyl alcohol in an attempt to avoid bed plugging arising from solids formation, but without a great deal of success. It was also independently observed that there was significant leaching of palladium from the catalyst bed into the reaction product mixture.

TABLE 2

| Effect of Palladium as Catalyst | | | | | |
|---|---|---|---|---|---|
| Peri- | Mole Ratio | Temp. | Conversion[b] | Selectivity | |
| od | EDA:ketone[a] | °C. | (mole %) | CEDA | DICEDA |
| 2 | 6:1 | 180 | 99.4 | 99.3 | 2.8 |
| 3 | 6:1 | 180 | 99.5 | 88.4 | 4.9 |
| 4 | 6:1 | 180 | 99.5 | 99.7 | 2.1 |
| 6 | 5:1 | 180 | 99.6 | 88.1 | 3.2 |
| 7 | 5:1 | 185 | 99.6 | 92.3 | 3.5 |
| 8 | 5:1 | 181 | 99.5 | 92.4 | 2.3 |
| 10 | 3:1 | 180 | 99.7 | 86.5 | 4.3 |
| 11 | 3:1 | 193 | 99.5 | 88.6 | 6.9 |
| 12 | 3:1 | 181 | 99.7 | 95.3 | 5.6 |
| 15 | 6:1 | 200 | 99.5 | 91.2 | 2.3 |
| 16 | 6:1 | 199 | 99.4 | 96.9 | 2.4 |
| 17 | 6:1 | 200 | 99.9 | 75.7 | 2.5 |
| 19 | 6:1 | 251 | 99.5 | 54.8 | 3.3 |
| 20 | 6:1 | 250 | 99.5 | 58.5 | 6.4 |
| 21 | 6:1 | 249 | 99.5 | 59.3 | 3.9 |
| 23 | 6:1 | 180 | 100.0 | 87.4 | 7.6 |
| 24 | 6:1 | 179 | 100.0 | 78.8 | 3.0 |
| 25 | 6:1 | 179 | 100.0 | 70.1 | 2.9 |

[a]Ketone was cyclohexanone.
[b]Conversion of cyclohexanone

EXAMPLE 5

Continuous preparation of N-cyclohexyl ethylenediamine

This run was performed using as a catalyst 0.8 weight percent palladium supported on charcoal, 4×8 mesh.

The results, summarized in Table 3, show the generally poor behaviour of the catalyst, especially with respect to selectivity as well as metal leaching. In all cases the feedstock was a premix having a mole ratio of 5:1 EDA:cyclohexanone and having a weight ratio of EDA:water of 4:1. Reaction temperatures were 179°–181° C.

TABLE 3

Effect of Palladium on Charcoal as Catalyst

| Period | Conversion (mole %) | Selectivity CEDA | DICEDA |
|---|---|---|---|
| 2 | 99.8 | 69.3 | 9.9 |
| 3 | 99.8 | 64.6 | 13.1 |
| 4 | 99.8 | 62.4 | 8.3 |
| 5 | 99.8 | 55.2 | 5.3 |
| 6 | 99.8 | 53.4 | 5.7 |
| 7 | 99.8 | 59.2 | 4.0 |

What is claimed is:

1. A method for the selective preparation of a high purity N-monoalkyl alkylenediamine comprising reacting at N-monoalkyl alkylenediamine-forming conditions in a partially aqueous environment a carbonyl-containing component which is a ketone or aldehyde, an unsubstituted alkylenediamine, and hydrogen in the presence of a supported zerovalent platinum hydrogenation catalyst to afford a first product mixture containing the N-monoalkyl alkylenediamine and a N,N'-dialkyl alkylenediamine, cooling the first product mixture and removing the N,N'-dialkyl alkylenediamine which separates to afford a second product mixture, removing from the second product mixture a) unreacted alkylenediamine and b) excess water, and collecting as a residue high purity N-monoalkyl alkylenediamine.

2. The method of claim 1 where the unsubstituted alkylenediamine forms an azeotrope with water and the partially aqueous environment contains water in an amount not more than that in said azeotrope.

3. The method of claim 2 where said unsubstituted alkylenediamine is initially present in a partially aqueous environment whose water content corresponds approximately to that of the azeotrope of said unsubstituted alkylenediamine with water.

4. The method of claim 1 where the first product mixture contains unreacted unsubstituted alkylenediamine and water in a proportion approximately the same as that in their azeotrope.

5. The method of claim 1 where the unsubstituted alkylenediamine has the formula $H_2N(CH_2)_xNH_2$, where x is an integer from 2 up to about 10.

6. The method of claim 5 where x is 2.

7. The method of claim 5 where x is from 3 to 6.

8. The method of claim 1 where the aldehyde or ketone is an aliphatic aldehyde or ketone containing from 3 to 10 carbon atoms.

9. The method of claim 2 where the carbonyl component is a cycloaliphatic ketone containing from 5 up to 10 carbon atoms.

10. The method of claim 9 where the ketone is cyclohexanone.

11. The method of claim 6 where the molar ratio of the alkylenediamine to the carbonyl component is from 1:1 to about 6:1.

12. The method of claim 11 where the molar ratio is 4.5:1 to about 5.5:1.

13. The method of claim 1 where the weight ratio of alkylenediamine to water in the partially aqueous environment is from about 10:1 to about 4:1.

14. The method of claim 1 where the imine-forming conditions include a temperature from about 150° to about 225° C.

15. The method of claim 14 where the temperature is from about 175° to about 200° C.

16. A continuous method for the selective preparation of N-cyclohexyl ethylenediamine containing not more than 5 weight percent of N,N'-dicylohexyl ethylenediamine comprising reacting at a temperature from about 150° to about 225° C. cyclohexanone with from 1 up to about 6 molar proportions of ethylenediamine in a partially aqueous environment whose weight ratio of ethylenediamine to water is from about 4:1 up to about 10:1 and hydrogen in the presence of a fixed mass of a supported zerovalent platinum hydrogenation catalyst to afford a first product mixture containing the N-cyclohexyl alkylenediamine and N,N'-dicyclohexyl ethylenediamine, cooling the first product mixture and removing the N,N'-dicyclohexyl ethylenediamine which separates to afford a second product mixture, removing from the second product mixture a) unreacted ethylenediamine, at least in part as its azeotrope with water, by distillation and b) excess water, and collecting as a residue high purity N-cyclohexyl alkylenediamine containing less than 5 weight percent N,N'-dicyclohexyl ethylenediamine.

17. The method of claim 16 where cyclohexanone is reacted with from 4.5 up to about 5.5 molar proportions of ethylenediamine.

18. The method of claim 16 where the temperature is from about 175° up to about 200° C.

19. The method of claim 16 where the unreacted ethylenediamine recovered at stage a) is recycled to react with cyclohexanone.

* * * * *